(12) United States Patent
Akui

(10) Patent No.: US 11,751,756 B2
(45) Date of Patent: Sep. 12, 2023

(54) ENDOSCOPE

(71) Applicant: OLYMPUS CORPORATION, Tokyo (JP)

(72) Inventor: Nobuaki Akui, Hino (JP)

(73) Assignee: OLYMPUS CORPORATION, Tokyo (JP)

( * ) Notice: Subject to any disclaimer, the term of this patent is extended or adjusted under 35 U.S.C. 154(b) by 433 days.

(21) Appl. No.: 17/150,422

(22) Filed: Jan. 15, 2021

(65) Prior Publication Data

US 2021/0161367 A1 Jun. 3, 2021

Related U.S. Application Data

(63) Continuation of application No. PCT/JP2018/031049, filed on Aug. 22, 2018.

(51) Int. Cl.
*A61B 1/00* (2006.01)
*A61B 1/005* (2006.01)
*A61B 1/06* (2006.01)

(52) U.S. Cl.
CPC .......... *A61B 1/0057* (2013.01); *A61B 1/0661* (2013.01)

(58) Field of Classification Search
CPC ... A61B 1/0057; A61B 1/0661; A61B 1/0004; A61B 1/00078; A61B 1/0008; A61B 1/0051; A61B 1/018; A61B 1/307; A61B 1/00071; A61B 1/0055
USPC ................... 600/146, 121, 144, 149
See application file for complete search history.

(56) References Cited

U.S. PATENT DOCUMENTS

| | | | |
|---|---|---|---|
| 6,013,024 | A | 1/2000 | Mitsuda et al. |
| 2007/0100200 | A1 | 5/2007 | Suzuki et al. |
| 2013/0205937 | A1 | 8/2013 | Arai |
| 2017/0065153 | A1 | 3/2017 | Fujitani |

FOREIGN PATENT DOCUMENTS

| | | |
|---|---|---|
| JP | 2-98901 U | 8/1990 |
| JP | 9-66021 A | 3/1997 |
| JP | 10-258022 A | 9/1998 |
| JP | 2007-054125 A | 3/2007 |
| JP | 2007-190361 A | 8/2007 |
| JP | 2009-018116 A | 1/2009 |
| JP | 2013-027466 A | 2/2013 |
| JP | 2016-187554 A | 11/2016 |
| WO | 2013/011771 A1 | 1/2013 |
| WO | 2016/047265 A1 | 3/2016 |

OTHER PUBLICATIONS

International Search Report dated Oct. 9, 2018 received in PCT/JP2018/031049.

*Primary Examiner* — Timothy J Neal
*Assistant Examiner* — James Edward Boice
(74) *Attorney, Agent, or Firm* — Scully, Scott, Murphy & Presser, P.C.

(57) ABSTRACT

An endoscope includes: an insertion section; an operation section; a bending portion; a longitudinal member for maintaining a constant distance from the operation section to a distal end portion of the insertion section along a longitudinal axis of the insertion section; and a flexible tube portion provided in a movable manner with respect to the operation section and the longitudinal member in a longitudinal axis direction, and making the bending portion extend and contract with movement of the flexible tube portion with respect to the operation section in the longitudinal axis direction.

9 Claims, 7 Drawing Sheets

ENDOSCOPE

CROSS REFERENCE TO RELATED APPLICATION

This application is a continuation application of PCT/JP2018/031049 filed on Aug. 22, 2018, the entire contents of which are incorporated herein by this reference.

BACKGROUND OF THE INVENTION

1. Field of the Invention

The present invention relates to an endoscope including an insertion section provided with a portion which bends passively.

2. Description of the Related Art

An endoscope for medical use includes an elongated insertion section which is insertable into a subject, and can perform observation of an inside of the subject and treatment using a treatment instrument or the like. As one of endoscopes for medical use, for example, there has been known an endoscope for renal pelvis and urinary organs (nephroscope) disclosed in Japanese Patent Application Laid-Open Publication No. 2016-187554.

As disclosed in Japanese Patent Application Laid-Open Publication No. 2016-187554, an insertion section of an endoscope for renal pelvis and urinary organs is inserted into a ureter of a subject through an access sheath. The access sheath is a tubular member. By holding the access sheath in the ureter in an inserted state, the repeated insertion and removal of the insertion section of the endoscope into and out from the ureter can be performed easily.

SUMMARY OF THE INVENTION

An endoscope according to an aspect of the present invention includes: an insertion section inserted into a subject; an operation section disposed on a proximal end side of the insertion section; a bending portion forming a portion of the insertion section, at least a portion of the bending portion being extendable and contractible in a longitudinal axis direction of the insertion section; a longitudinal member configured to maintain a constant distance from the operation section to a distal end portion of the insertion section along the longitudinal axis of the insertion section; and a flexible tube portion forming a portion of the insertion section, disposed on a proximal end side with respect to the bending portion, provided in a movable manner with respect to the operation section and the longitudinal member in the longitudinal axis direction, and configured to make the bending portion extend and contract with movement of the flexible tube portion with respect to the operation section in the longitudinal axis direction.

DETAILED DESCRIPTION OF THE PREFERRED EMBODIMENTS

Figure 1:
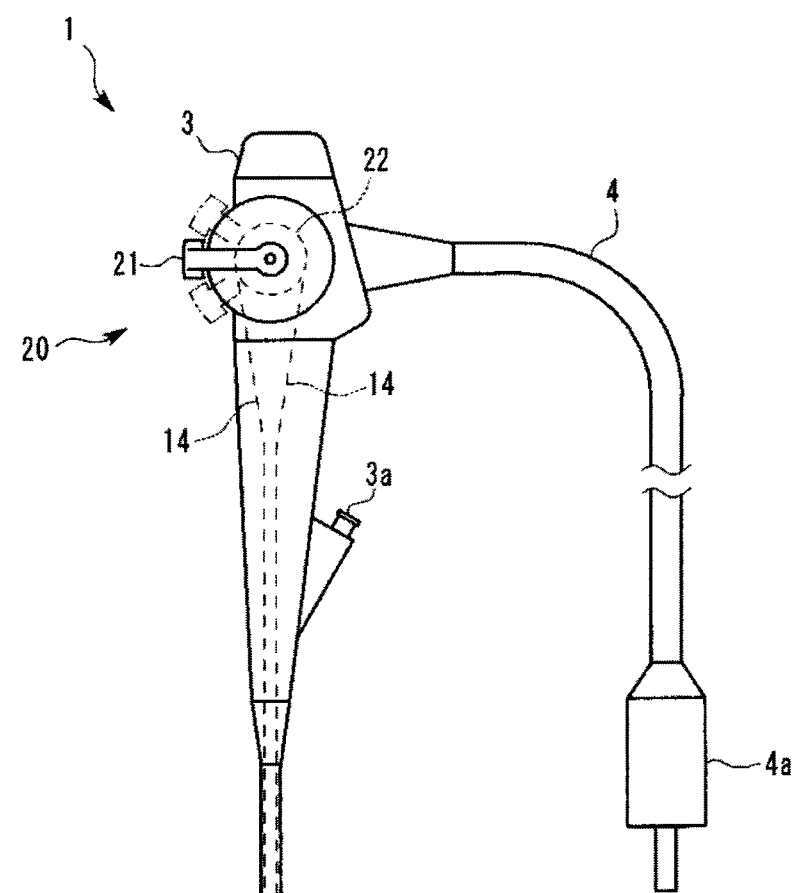
FIG. 1 is a view showing a schematic configuration of an endoscope according to a first embodiment.

Hereinafter, preferred embodiments of the present invention are described with reference to drawings. In the respective drawings used in the description made hereinafter, for the sake of setting sizes of respective components legible in the drawings, the scales of the respective components are made different from each other. The present invention is not limited to the number and the amounts of components, the shapes of the components, the ratios between the sizes of the components, and the relative positional relationships among the respective components described in the drawings.

First Embodiment

An endoscope 1 shown in FIG. 1 includes an elongated insertion section 2 which is insertable into a subject such as a human body, and the insertion section 2 has a configuration for observing the inside of the subject. The subject into which the insertion section 2 of the endoscope 1 is inserted is not limited to a human body, but may be other living bodies or an artificial object such as a machine or a building.

In the embodiment, as an example, the subject is a human body. In the embodiment, as an example, the endoscope 1 is an endoscope for renal pelvis and urinary organs (nephroscope). In the embodiment, as an example, the endoscope 1 is configured as a so-called videoscope.

The endoscope 1 includes: the insertion section 2 which is long along a predetermined axis; an operation section 3 which is positioned on a proximal end which is one end of the insertion section 2; and a universal cord 4 which extends from the operation section 3.

The operation section 3 is a part which a user grasps. In the operation section 3, a treatment instrument insertion opening 3a and a bending operation portion 20 are disposed. A connector 4a which is connected to an external apparatus not shown is provided to the universal cord 4.

Hereinafter, with respect to the insertion section 2, the predetermined axis which is disposed parallel to a longitudinal direction is referred to as a longitudinal axis L. As described previously, the proximal end of the insertion section 2 is connected to the operation section 3. The other end of the insertion section 2 on a side opposite to the proximal end is referred to as a distal end.

Figure 2:
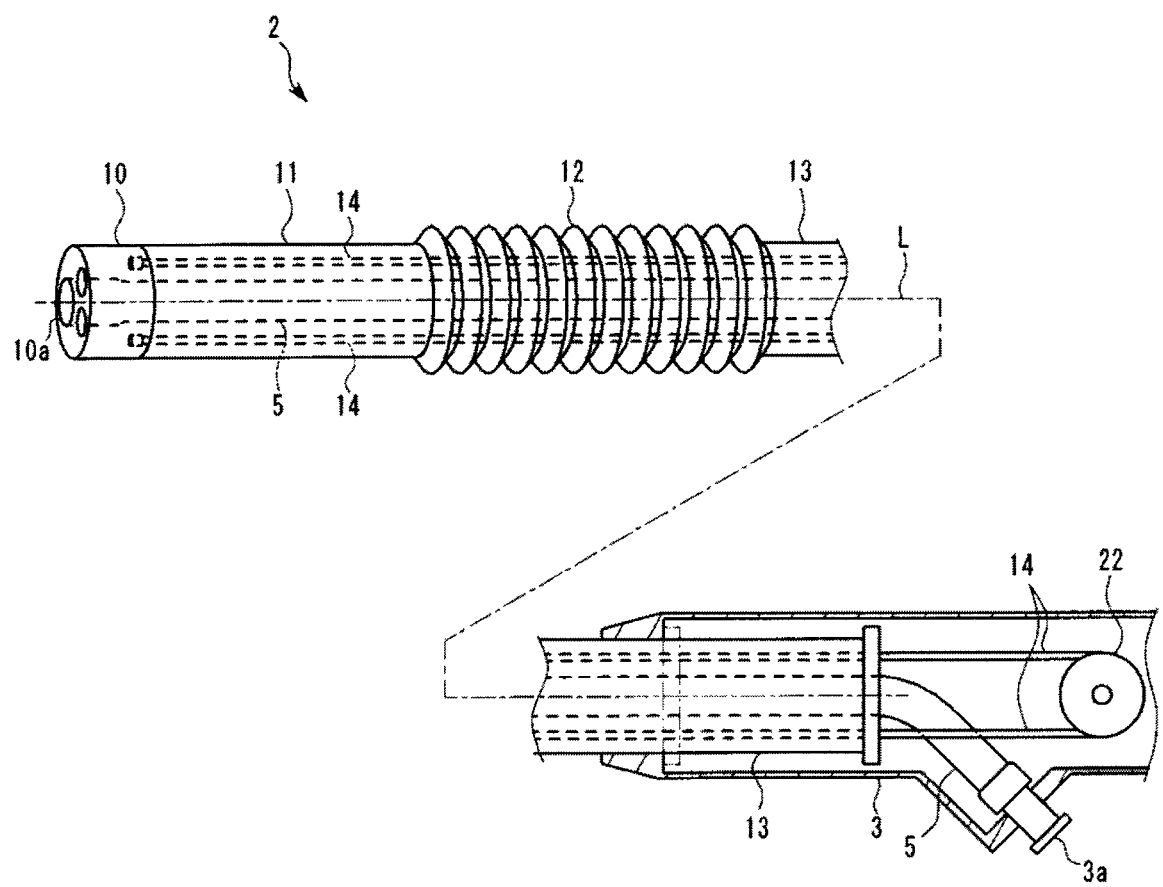
FIG. 2 is a view showing a configuration of an insertion section according to the first embodiment.

As shown in FIG. 2, the insertion section 2 includes a distal end portion 10, a first bending portion 11, a second bending portion 12, and a flexible tube portion 13. The distal end portion 10, the first bending portion 11, the second bending portion 12 and the flexible tube portion 13 are connected to each other in this order from the distal end toward the proximal end along the longitudinal axis L of the insertion section 2.

The distal end portion 10 is disposed on the distal end of the insertion section 2. An image pickup unit, an illumination light irradiation member and a channel opening 10a are disposed in the distal end portion 10.

The image pickup unit is an apparatus for picking up an optical image. The image pickup unit includes an objective lens and an image pickup device. A portion of the image pickup unit may be disposed in the operation section 3. For example, the image pickup unit may be configured to include: an objective lens disposed in the distal end portion 10; an image pickup device disposed in the operation section 3; and an image guide fiber which is inserted through the insertion section 2.

The image pickup unit is electrically connected to the connector 4a via an electric cable disposed in the endoscope 1. When the connector 4a is connected to an external apparatus, the image pickup unit is electrically connected to the external apparatus. The external apparatus includes a processor which displays an optical image picked up by the image pickup unit on a display apparatus not shown.

The illumination light irradiation member irradiates light which illuminates an object by the image pickup unit. A light source for supplying light irradiated from the illumination light irradiation member may be disposed in the endoscope 1, or may be disposed in the external apparatus. The image pickup unit and the illumination light irradiation member of the endoscope 1 are known techniques and hence, the detailed description of the image pickup unit and the illumination light irradiation member is omitted.

The channel opening 10a communicates with a distal end of a longitudinal member 5 which is formed of a tube. A proximal end of the longitudinal member 5 communicates with the treatment instrument insertion opening 3a formed in the operation section 3. Accordingly, the longitudinal member 5 is inserted through the insertion section 2 and the operation section 3. A distal end of the longitudinal member 5 is fixed to the distal end portion 10 of the insertion section 2. A portion of the longitudinal member 5 positioned in the operation section 3 is fixed to the operation section 3. The longitudinal member 5 has flexibility so as to be bendable following bending of the insertion section 2. Although described in detail later, the longitudinal member 5 has rigidity in a predetermined compression direction. In the embodiment, as an example, the longitudinal member 5 is formed of a tube. However, the longitudinal member 5 may be formed of a columnar member which is not hollow. The endoscope 1 may include a plurality of longitudinal members 5.

The first bending portion 11 is disposed on a proximal end side of the distal end portion 10. The first bending portion 11 actively bends in response to an operation of the bending operation portion 20 performed by a user. A plurality of wires 14 are inserted through the insertion section 2. Distal ends of the individual wires 14 are fixed to the first bending portion 11 in a vicinity of the distal end of the first bending portion 11. The first bending portion 11 has flexibility, and a bent shape of the first bending portion 11 changes corresponding to a towing amount in a direction toward proximal ends of the plurality of wires 14.

The proximal ends of the plurality of wires 14 are connected to a towing mechanism portion 22 disposed in the operation section 3. The towing mechanism portion 22 performs towing and slackening of the plurality of wires 14 in response to an operation of the bending operation portion 20 by a user. The technique for actively bending the insertion section of the endoscope is known and hence, the detailed description of the technique is omitted.

In the embodiment, as an example, the bending operation portion 20 is a lever which relatively moves in two directions with respect to the operation section 3. In the embodiment, as an example, the towing mechanism portion 22 tows and slackens two wires 14 in response to movement of the lever. In the embodiment, as an example, the first bending portion 11 actively bends in two directions in response to towing and slackening of the two wires 14. The first bending portion 11 may be configured to bend in four directions.

The second bending portion 12 is disposed on a proximal end side of the first bending portion 11. The second bending portion 12 has flexibility, and passively bends in response to an external force. The second bending portion 12 extends and contracts in a direction along the longitudinal axis L. The configuration which allows the second bending portion 12 to extend and contract in the direction along the longitudinal axis L is not particularly limited. As shown in FIG. 2, in the embodiment, as an example, an outer peripheral member of the second bending portion 12 is configured by a bellows. In such a configuration, the outer peripheral member is a structural member of the second bending portion 12, and is a member in which one or a plurality of conduits are formed in a penetrating manner in a direction along the longitudinal axis L. The wires 14, the longitudinal member 5, electric cables and the like are inserted through one or a plurality of conduits which the outer peripheral member includes. An outer peripheral member of the first bending portion 11 may also be configured by a bellows in the same manner as the second bending portion 12.

The second bending portion 12 exhibits a lower rigidity than the longitudinal member 5 and the wires 14 against a force in a direction along the longitudinal axis L. In other words, the longitudinal member 5 has a higher rigidity in a compression direction than the second bending portion 12. The wires 14 have a higher rigidity in an extending direction than the second bending portion 12.

The flexible tube portion 13 is disposed on a proximal end side of the second bending portion 12. The flexible tube portion 13 has flexibility, and passively bends in response to an external force. The flexible tube portion 13 has a higher rigidity than the second bending portion 12 against a force in a direction along the longitudinal axis L. In other words, when a compression force in a direction along the longitudinal axis L is applied to the insertion section 2, a deformation amount of the flexible tube portion 13 is smaller than a deformation amount of the second bending portion 12.

The flexible tube portion 13 is provided in a movable manner in a direction along the longitudinal axis L with respect to the operation section 3, the wires 14 and the longitudinal member 5. A force which moves the flexible tube portion 13 with respect to the operation section 3 may be generated by a user, or may be generated by an electrically operated actuator.

In the embodiment, as an example, the flexible tube portion 13 moves in the direction along the longitudinal axis L with respect to the operation section 3 by a force which a user generates. More specifically, when the user grasps the operation section 3 with one hand, and applies a force in the direction along the longitudinal axis L to the flexible tube portion 13 with the other hand, the flexible tube portion 13 moves in the direction along the longitudinal axis L with respect to the operation section 3. At this stage of the operation, the wires 14 are connected to the towing mechanism portion 22 disposed in the operation section 3 and hence, the flexible tube portion 13 moves in the direction along the longitudinal axis L with respect to the wires 14. In the same manner, the longitudinal member 5 is fixed to the operation section 3 and hence, the flexible tube portion 13 moves in the direction along the longitudinal axis L with respect to the longitudinal member 5. The flexible tube portion 13 moves with respect to the operation section 3 independently from internal components such as the electric cables inserted through the insertion section 2.

Even when the flexible tube portion 13 moves in the direction along the longitudinal axis L with respect to the operation section 3, a distance from the operation section 3 to the distal end of the insertion section 2 along the longitudinal axis L of the insertion section 2 does not change. More specifically, in the embodiment, when the flexible tube portion 13 moves toward the distal end with respect to the operation section 3, a force in the extending direction is applied to the wires 14. However, the wires 14 have rigidity which maintains a distance from the operation section 3 to the first bending portion 11 along the longitudinal axis L of the insertion section 2. Accordingly, when the flexible tube portion 13 moves toward the distal end with respect to the operation section 3, as shown in FIG. 3, the second bending portion 12 is compressed in the direction along the longitudinal axis L.

Figure 3:
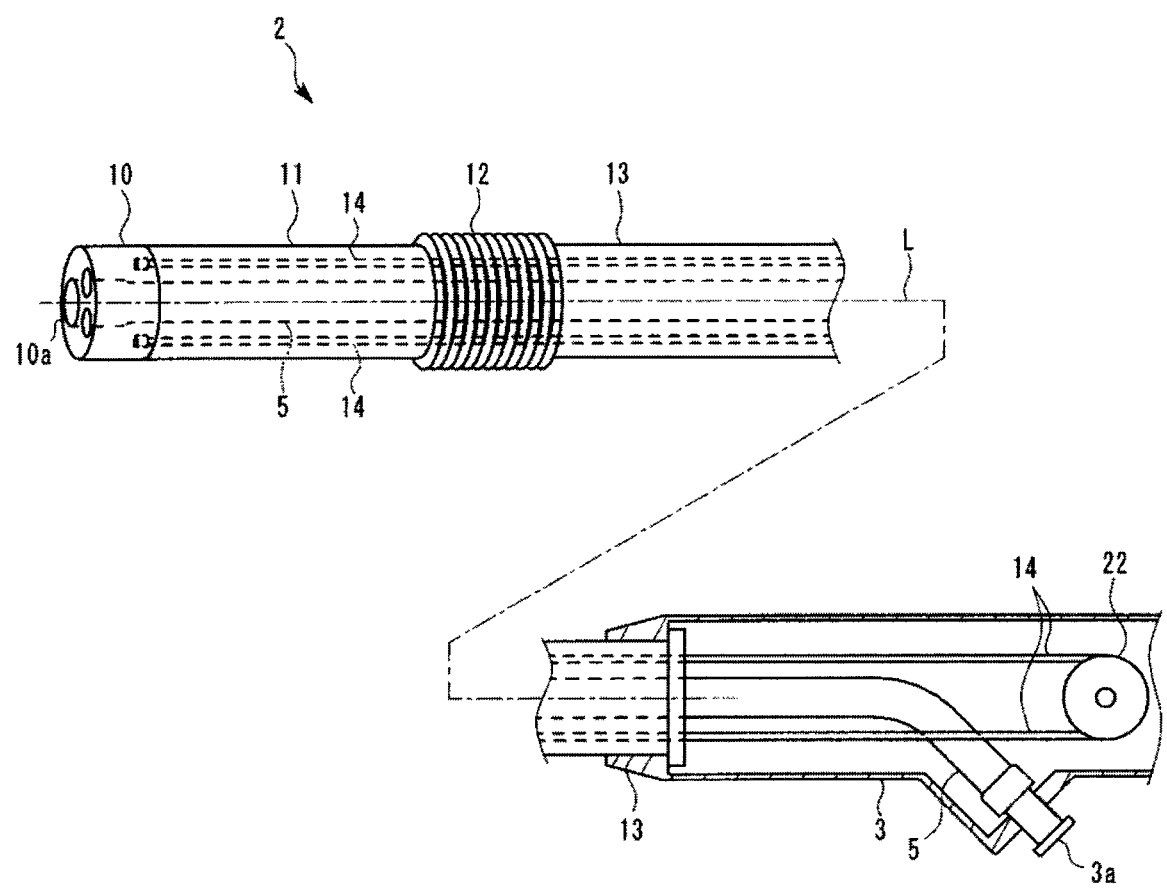
FIG. 3 is a view showing the insertion section according to the first embodiment in a state where a second bending portion is compressed.

On the other hand, when the flexible tube portion 13 moves toward the proximal end with respect to the operation section 3 from a state shown in FIG. 3, a force in a compression direction is applied to the longitudinal member 5. However, the longitudinal member 5 has rigidity which maintains the length without buckling deformation. In other words, when the flexible tube portion 13 moves toward the proximal end side, the longitudinal member 5 maintains a distance from the operation section 3 to the first bending portion 11 along the longitudinal axis of the insertion section 2. Accordingly, when the flexible tube portion 13 moves toward the proximal end with respect to the operation section 3, as shown in FIG. 2, the second bending portion 12 extends in the direction along the longitudinal axis L.

In the embodiment, bending rigidity of the second bending portion 12 in a state where a length of the second bending portion 12 is longest is lower than bending rigidity of the flexible tube portion 13. In the embodiment, bending rigidity indicates difficulty in deformation when the second bending portion 12 extending along the longitudinal axis L is deformed by bending. The larger the bending rigidity, the smaller a deformation amount in the bending direction becomes.

In the endoscope 1 according to the embodiment, when a user moves the flexible tube portion 13 in the direction along the longitudinal axis L, the length of the second bending portion 12 changes. In a first state (FIG. 2) where the flexible tube portion 13 is positioned on a most proximal end side, bending rigidity of the second bending portion 12 is maintained at a value lower than bending rigidity of the flexible tube portion 13. On the other hand, in a second state (FIG. 3) where the flexible tube portion 13 is positioned on a most distal end side, the second bending portion 12 is compressed in the direction along the longitudinal axis L and hence, bending rigidity of the second bending portion 12 becomes higher than the bending rigidity in the first state.

In the endoscope 1 according to the embodiment having the configuration described above, when a distal end of the insertion section 2 is inserted into an inlet of an access sheath, the second bending portion 12 is compressed so that bending rigidity of the second bending portion 12 is increased whereby the insertion section 2 can be easily inserted into the access sheath.

In the endoscope 1 according to the embodiment, a distal end of the insertion section 2 is inserted into the access sheath and, thereafter, the second bending portion 12 is extended so that bending rigidity of the second bending portion 12 is lowered. Accordingly, the insertion section 2 in a subject can be easily handled.

The endoscope 1 according to the embodiment described above is configured such that a user directly grasps the flexible tube portion 13 and moves the flexible tube portion 13. However, the endoscope 1 may have a rotatable dial on the operation section 3, and may have a mechanism which converts a rotational force of the dial into a force which moves the flexible tube portion 13.

Figure 4:
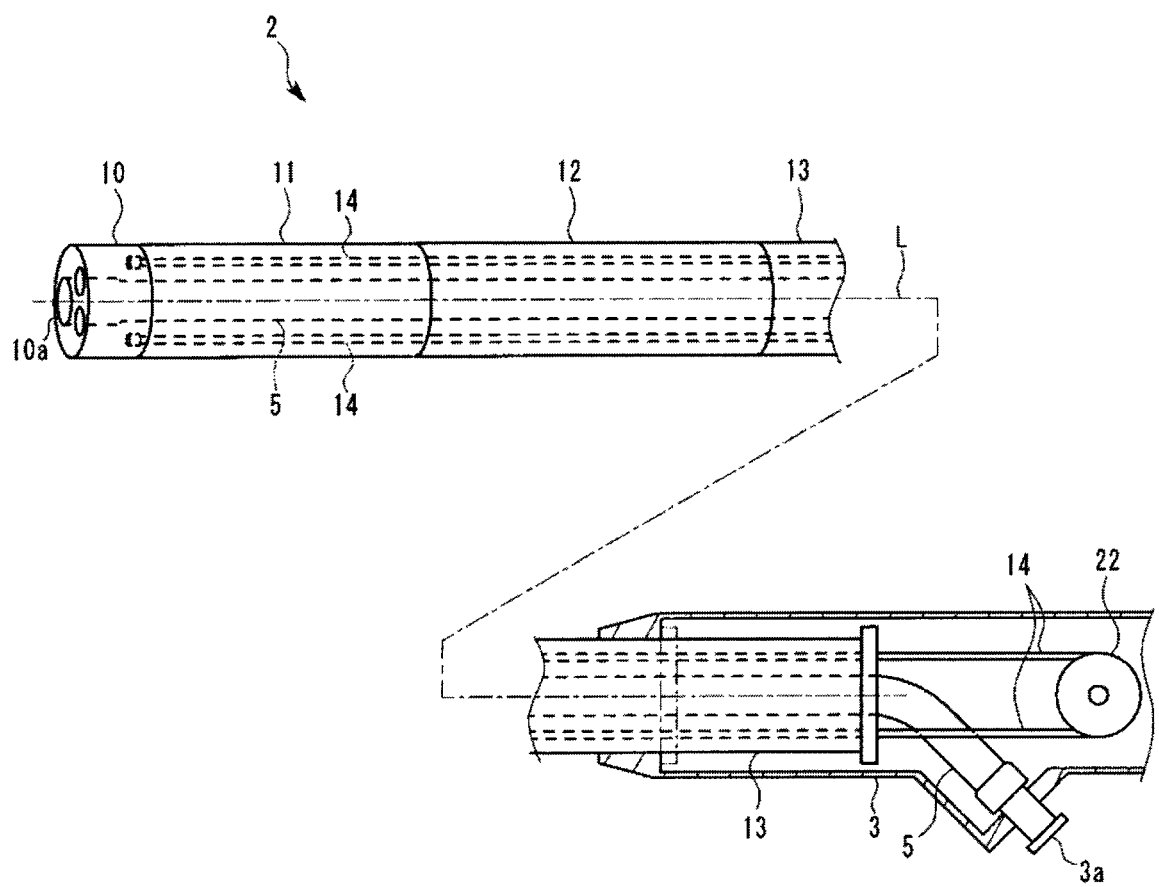
FIG. 4 is a view showing a configuration of an insertion section according to a modification of the first embodiment.
Figure 5:
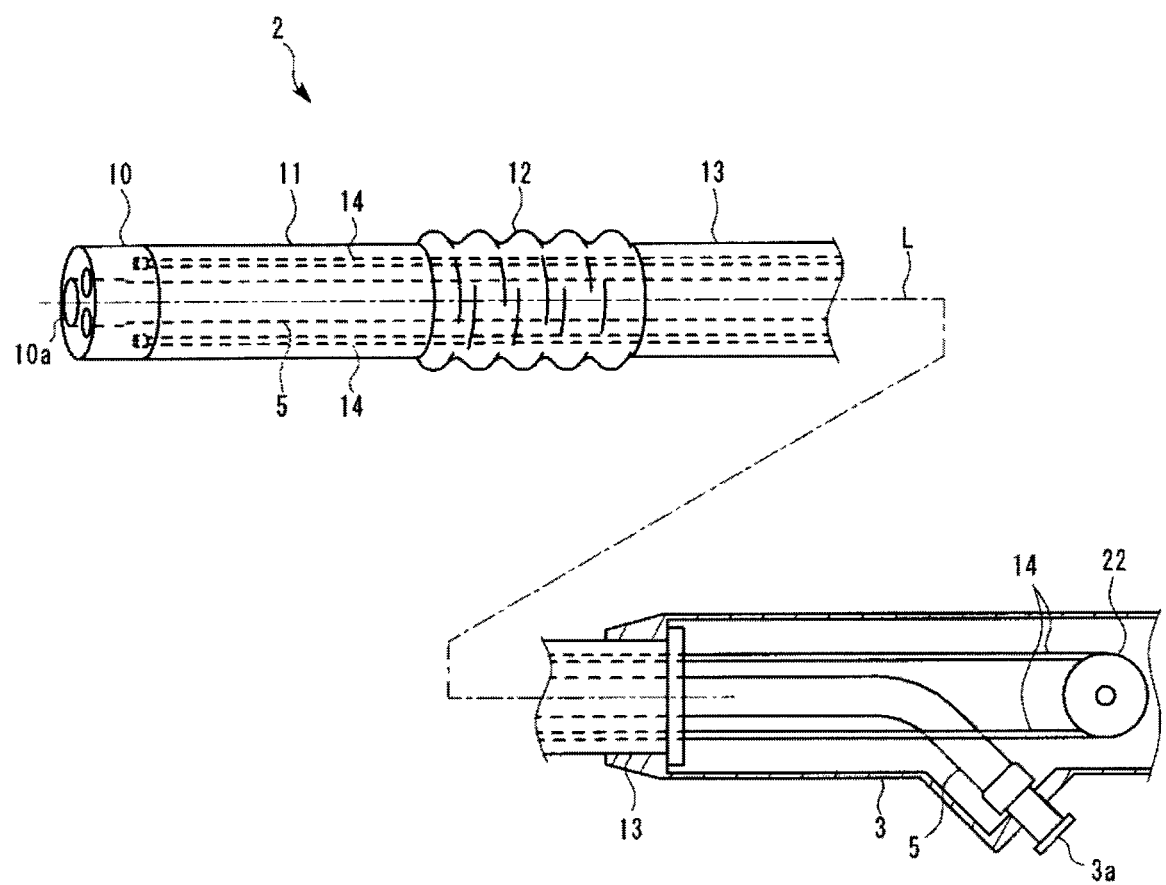
FIG. 5 is a view showing the insertion section according to the modification of the first embodiment in a state where a second bending portion is compressed.

In the embodiment described above, the second bending portion 12 is configured by a bellows. However, it is sufficient that the second bending portion 12 is extendable and contractible in the direction along the longitudinal axis L. FIG. 4 and FIG. 5 show a modification of the second bending portion 12.

The second bending portion 12 of the modification shown in FIG. 4 and FIG. 5 is formed of a tubular member which is flexible and elastically deformable. In the modification, in a first state (FIG. 4) where a flexible tube portion 13 is positioned on a most proximal end side, and a length of the second bending portion 12 is longest, an outer surface of the second bending portion 12 is smooth. On the other hand, in a second state (FIG. 5) where the flexible tube portion 13 is positioned on a most distal end side, and the length of the second bending portion 12 is shortest, wrinkles are formed on the outer surface of the second bending portion 12.

Bending rigidity of the second bending portion 12 can also be enhanced in the modification, in the same manner as the embodiment described previously, by compressing the second bending portion 12 in a direction along a longitudinal axis L. Accordingly, also in the endoscope 1 according to the modification, the insertion section 2 can be easily inserted into an access sheath.

Second Embodiment

Hereinafter, a second embodiment of the present invention is described. Hereinafter, only components which make the second embodiment differ from the first embodiment are described, and components which are identical with the corresponding components in the first embodiment are given with the same symbols, and the description of such components is omitted when desired.

Figure 6:
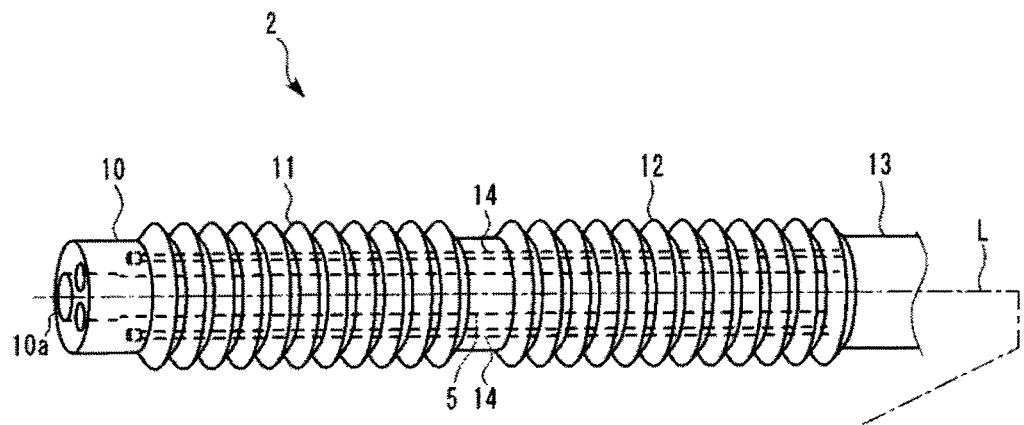
FIG. 6 is a view showing a configuration of an insertion section according to a second embodiment.
Figure 6:
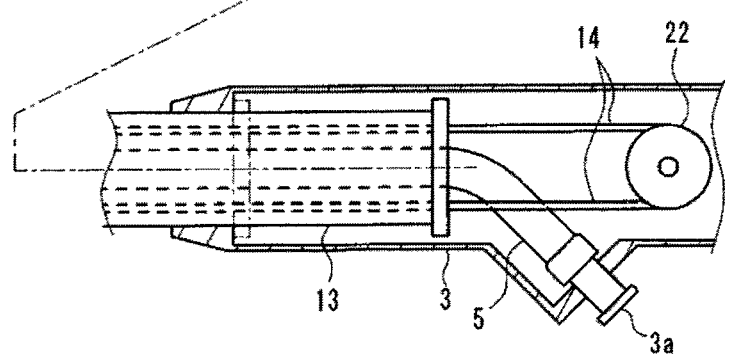

FIG. 6 is a view showing a configuration of an insertion section 2 of an endoscope 1 according to the second embodiment. A first bending portion 11 of the insertion section 2 of the embodiment extends and contracts in a direction along a longitudinal axis L. The configuration which allows the first bending portion 11 to extend and contract in the direction along the longitudinal axis L is not particularly limited. As shown in FIG. 6, in the embodiment, as an example, an outer peripheral member of the first bending portion 11 is configured by a bellows in the same manner as a second bending portion 12.

In the endoscope 1 according to the embodiment, when a user moves a flexible tube portion 13 in the direction along the longitudinal axis L, a length of the first bending portion 11 and a length of the second bending portion 12 change. In a state where the flexible tube portion 13 is positioned on a most distal end side, the first bending portion 11 and the second bending portion 12 are compressed in the direction along the longitudinal axis L and hence, bending rigidity of the first bending portion and bending rigidity of the second bending portion 12 are increased.

When an outer peripheral member of the first bending portion 11 is configured by a bellows as in the case of the embodiment, it is difficult to provide a configuration which restricts a direction of bending deformation to the first bending portion 11. The configuration which restricts the direction of the bending deformation may be configured by a plurality of bending pieces which are disposed on a bending portion of a conventional endoscope, for example. Accordingly, in a state where the flexible tube portion 13 is positioned on a most proximal end side, the first bending portion 11 of the embodiment is liable to generate bending deformation in a direction different from a direction that the first bending portion 11 is bent due to towing of wires 14 caused by gravity or the like. Accordingly, in the endoscope 1 according to the embodiment, when a distal end of the insertion section 2 is inserted into an inlet of an access sheath, the first bending portion 11 is compressed so that bending rigidity of the first bending portion 11 is increased whereby a deformation amount of the first bending portion 11 can be suppressed.

As described above, in the endoscope 1 according to the embodiment, when the distal end of the insertion section 2 is inserted into the inlet of the access sheath, bending rigidity of the first bending portion 11 and bending rigidity of the second bending portion 12 are increased and hence, the insertion section 2 can be easily inserted into the access sheath.

Third Embodiment

Hereinafter, a third embodiment of the present invention is described. Hereinafter, only components which make the third embodiment differ from the first embodiment are described, and components which are identical with the corresponding components in the first embodiment are given with the same symbols, and the description of such components is omitted when desired.

Figure 7:
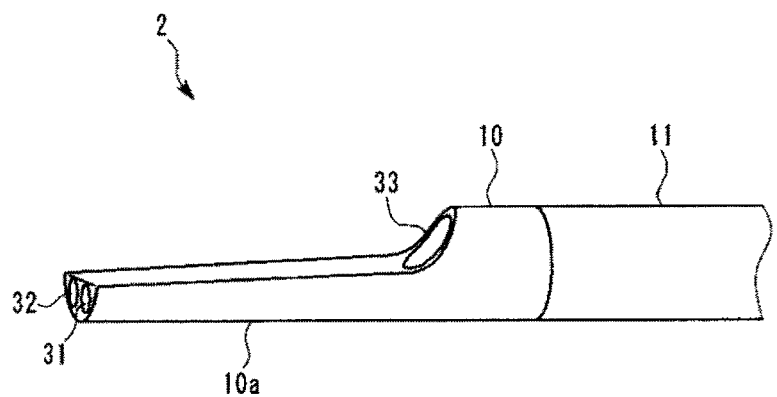
FIG. 7 is a view showing a distal end portion of an insertion section according to a third embodiment.

FIG. 7 is a perspective view showing a distal end portion 10 of an insertion section 2 of an endoscope 1 according to the third embodiment. As shown in FIG. 7, an image pickup unit 31, an illumination light irradiation member 32 and a channel opening 33 are disposed on the distal end portion 10.

In the embodiment, an image pickup unit 31 and an illumination light irradiation member 32 are mounted on a distal end side with respect to the channel opening 33. In other words, the image pickup unit 31 and the illumination light irradiation member 32 are disposed on a protruding portion 10a protruding toward a distal end side with respect to the channel opening 33.

A tube is not disposed in the protruding portion 10a and hence, the protruding portion 10a has a smaller diameter than a proximal end of the distal end portion 10. In other words, a cross-sectional area of the protruding portion 10a on a plane orthogonal to a longitudinal axis L is smaller than a cross-sectional area of the proximal end of the distal end portion 10. The protruding portion 10a has a portion which is elastically deformable and hence, the protruding portion 10a is bendable.

In the endoscope 1 according to the embodiment, in a state where the insertion section 2 is inserted into a ureter, the elongated protruding portion 10a bends along a shape of the ureter. Accordingly, in the endoscope 1 according to the embodiment, a user can make the insertion section 2 easily advance in the ureter by pushing in a distal end direction.

Fourth Embodiment

Hereinafter, a fourth embodiment of the present invention is described. Hereinafter, only components which make the fourth embodiment differ from the third embodiment are described, and components which are identical with the corresponding components in the third embodiment are given with the same symbols, and the description of such components is omitted when desired.

Figure 8:
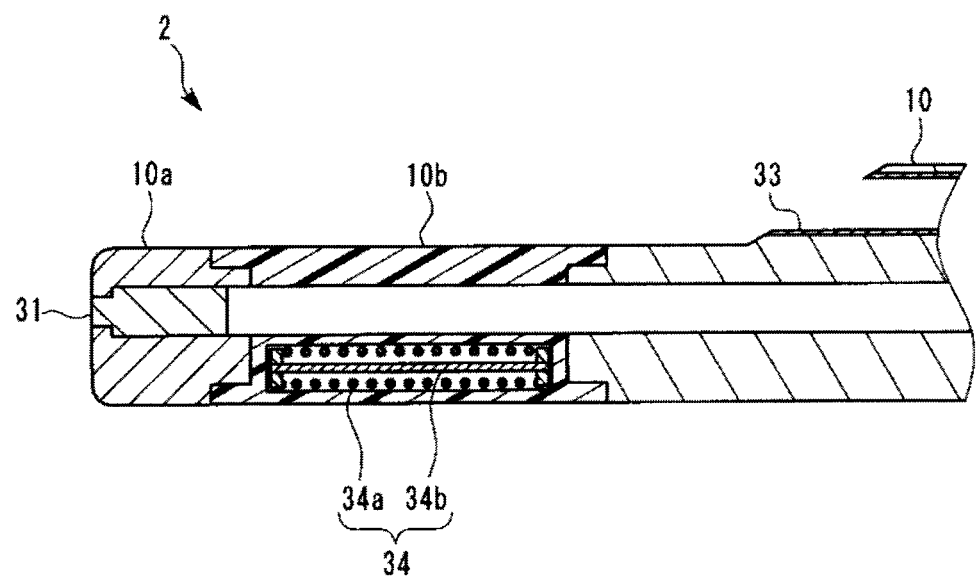
FIG. 8 is a partial cross-sectional view of a distal end portion of an insertion section according to a fourth embodiment.

FIG. 8 is a partial cross-sectional view of a distal end portion 10 of an insertion section 2 of an endoscope 1 according to the fourth embodiment. As has been described in the third embodiment, a protruding portion 10a protruding toward a distal end side with respect to a channel opening 33 is disposed on the distal end portion 10.

A bendable third bending portion 10b is disposed on a portion of the protruding portion 10a. An outer surface of the third bending portion 10b is formed of a resin or the like which is elastically deformable. An image pickup unit 31 and an illumination light irradiation member 32 (not shown) are mounted on the protruding portion 10a.

In the embodiment, a rigidity changing mechanism 34 is disposed inside the third bending portion 10b.

The rigidity changing mechanism 34 includes a coil 34a and a bio metal fiber 34b. The coil 34a is wound around the bio metal fiber 34b about an axis parallel to a longitudinal axis L. The bio metal fiber 34b is a linear member made of a material which contracts when electricity is supplied to the material.

The bio metal fiber 34b is inserted through the coil 34a. Both ends of the coil 34a are fixed to the bio metal fiber 34b. In other words, when the bio metal fiber 34b contracts, the coil 34a is compressed.

The bio metal fiber 34b is electrically connected to an electricity supply cable not shown. The supply of electricity to the bio metal fiber 34b is switched by a switch mounted on an operation section 3.

The rigidity changing mechanism 34 having the configuration described above can make the bending rigidity of the third bending portion 10b when electricity is supplied to the bio metal fiber 34b higher than the bending rigidity of the third bending portion 10b when electricity is not supplied to the bio metal fiber 34b.

Accordingly, in the endoscope 1 according to the embodiment, by switching the supply of electricity to the bio metal fiber 34b between a supply state and a non-supply state, bending rigidity of the third bending portion 10b of the protruding portion 10a can be changed.

In the endoscope 1 according to the embodiment, by bringing the protruding portion 10a into a state where rigidity of the protruding portion 10a is increased, the insertion section 2 can be easily inserted into an access sheath.

The present invention is not limited to the above-mentioned embodiments, and modifications can be made without departing from the gist or the concept of the present invention readable from claims and the entire specification, and endoscopes which include such modifications also fall within the technical scope of the present invention.

What is claimed is:
1. An endoscope comprising:
an insertion section inserted into a subject;
an operation section disposed on a proximal end side of the insertion section;
a bending portion forming a portion of the insertion section, at least a portion of the bending portion being extendable and contractible in a longitudinal axis direction of the insertion section;
a longitudinal member configured to maintain a constant distance from the operation section to a distal end portion of the insertion section along the longitudinal axis of the insertion section; and a flexible tube portion forming a portion of the insertion section, disposed on a proximal end side with respect to the bending portion, provided in a movable manner with respect to the operation section and the longitudinal member in the longitudinal axis direction, and configured to make the bending portion extend and contract with movement of the flexible tube portion with respect to the operation section in the longitudinal axis direction.

2. The endoscope according to claim 1, wherein a plurality of wires are inserted through the insertion section, and the bending portion includes:

a first bending portion forming a portion of the insertion section, and configured to actively bend in response to towing of the wires; and a second bending portion forming a portion of the insertion section, disposed on a proximal end side with respect to the first bending portion, and configured to passively bend in response to an external force.

3. The endoscope according to claim 1, wherein the longitudinal member is inserted through the insertion section and the operation section, one end of the longitudinal member is fixed to the distal end portion of the insertion section, and another end of the longitudinal member is fixed to the operation section, and rigidity of the longitudinal member in a compression direction is higher than rigidity of the bending portion in the compression direction.

4. The endoscope according to claim 2, wherein the second bending portion is configured by a bellows.

5. The endoscope according to claim 4, wherein the first bending portion is also configured by a bellows.

6. The endoscope according to claim 1, wherein at least a portion of the bending portion is configured by a tubular member which is flexible and elastically deformable.

7. The endoscope according to claim 1, wherein a distal end of the insertion section includes a bendable protruding portion protruding toward a distal end side with respect to a channel opening, an image pickup unit and an illumination light irradiation member are mounted on the protruding portion, and the protruding portion has a portion which is elastically deformable.

8. The endoscope according to claim 7, wherein a bendable third bending portion is disposed on a portion of the protruding portion, a rigidity changing mechanism is disposed on the third bending portion, and the rigidity changing mechanism is configured to change bending rigidity of the third bending portion of the protruding portion with a supply of electricity.

9. The endoscope according to claim 8, wherein the rigidity changing mechanism includes:

a coil; and a bio metal fiber which is inserted through the coil, and the rigidity changing mechanism is configured to be able to change rigidity of the third bending portion in a state where the bio metal fiber contracts with a supply of electricity so that the coil is compressed.

* * * * *